(12) United States Patent
Rapoport

(10) Patent No.: US 9,759,673 B2
(45) Date of Patent: Sep. 12, 2017

(54) MAGNETIC RESONANCE-BASED SYSTEMS FOR DETECTING CONTAMINATING PARTICLES AND METHODS THEREOF

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 1108 days.

(21) Appl. No.: 13/906,803

(22) Filed: May 31, 2013

(65) Prior Publication Data

US 2014/0103926 A1    Apr. 17, 2014

Related U.S. Application Data

(60) Provisional application No. 61/712,284, filed on Oct. 11, 2012.

(51) Int. Cl.
*G01V 3/00* (2006.01)
*G01N 24/08* (2006.01)
*G01R 33/56* (2006.01)

(52) U.S. Cl.
CPC ........... *G01N 24/08* (2013.01); *G01N 24/084* (2013.01); *G01N 24/085* (2013.01); *G01R 33/5608* (2013.01)

(58) Field of Classification Search
USPC ....................................................... 324/309
See application file for complete search history.

(56) References Cited

U.S. PATENT DOCUMENTS

| | | | |
|---|---|---|---|
| 5,168,226 A | 12/1992 | Hinks | |
| 5,479,925 A | 1/1996 | Dumoulin et al. | |
| 5,596,275 A * | 1/1997 | Dechene | G01N 24/085 324/307 |
| 5,675,253 A * | 10/1997 | Smith | G01R 33/4625 324/306 |
| 5,705,928 A * | 1/1998 | Haner | G01R 33/307 324/320 |
| 6,380,737 B1 * | 4/2002 | Myles | G01R 33/307 324/306 |
| 6,737,864 B2 * | 5/2004 | Prammer | G01V 3/32 324/300 |
| 7,764,064 B2 * | 7/2010 | Reiss | G01R 33/30 324/307 |

(Continued)

*Primary Examiner* — Rodney Fuller
(74) *Attorney, Agent, or Firm* — Pearl Cohen Zedek Latzer Baratz LLP

(57) ABSTRACT

The present invention provides an MRI-based hazard screening system for detecting contaminating particles within or on the surface of an object, the system characterized by
 a. a sampling environment adapted for at least partially confining said object; said sampling environment is in fluid communication with at least one inlet and at least one fluid outlet;
 b. a fluid streamer for streaming a fluid, throughout said at least one inlet, towards said sampling environment where said fluid effectively interfaces said object; and further throughout said at least one outlet;
 c. an MRI device in fluid communication with said at least one outlet, adapted for providing an image of said particles streamed by said fluid thereby screening the presence of said particles within or on the surface of said object.

14 Claims, 7 Drawing Sheets

(56) References Cited

U.S. PATENT DOCUMENTS

| | | | |
|---|---|---|---|
| 8,766,631 B2* | 7/2014 | Hofmann | G01R 33/282 324/307 |
| 2004/0169512 A1 | 9/2004 | Jara | |
| 2009/0115416 A1* | 5/2009 | White | G01N 24/08 324/316 |
| 2009/0167322 A1* | 7/2009 | Magnuson | G01N 24/08 324/642 |
| 2012/0062226 A1* | 3/2012 | Pielak | G01R 33/307 324/309 |
| 2014/0167756 A1* | 6/2014 | Cho | G01R 33/30 324/309 |
| 2015/0253454 A1* | 9/2015 | Song | G01R 33/307 324/309 |
| 2016/0116540 A1* | 4/2016 | Zheng | G01R 31/3606 324/322 |

* cited by examiner

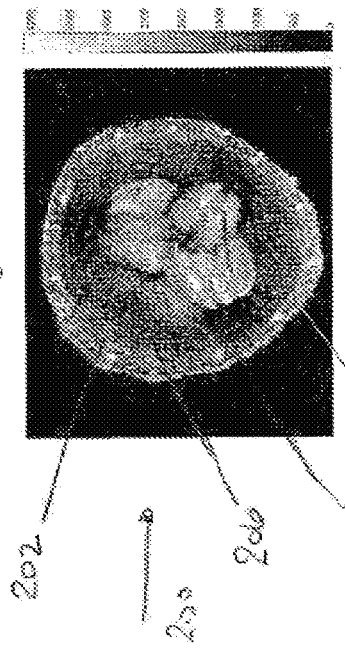

MAGNETIC RESONANCE-BASED SYSTEMS FOR DETECTING CONTAMINATING PARTICLES AND METHODS THEREOF

CROSS-REFERENCE TO RELATED APPLICATIONS

This application claims priority from U.S. Provisional Patent Application No. 61/712,284, filed on Oct. 11, 2012, which is hereby incorporated by reference.

FIELD OF THE INVENTION

The present invention generally pertains to a system and method for high resolution high contrast MRI for detecting contaminating particles within or on the surface of an object.

BACKGROUND OF THE INVENTION

It has long been known that low-field MRI produces high contrast images, but the weak field leads to a low signal to noise (S/N) ratio at poor resolution. Increasing the field increases the S/N ratio and, therefore, the resolution but decreases the contrast, so that high-field images have high resolution but poor contrast. There have been many attempts to overcome this limitation and to provide high-contrast high-resolution MRI images.

U.S. Pat. No. 5,168,226A to Hinks discloses a method whereby the total scan time may be shortened without losing resolution. The method disclosed in U.S. Pat. No. 516,226A comprises executing a fast spin echo pulse sequence in which a plurality of views are acquired and the fast spin echo pulse sequence is employed to acquire views from a plurality of separate images during a scan. The low-order phase encoding views are acquired for each image and stored in separate image data arrays, whereas the high-order phase encoding views are acquired only once and stored in all of the image data arrays. Each image data array is employed to reconstruct a separate image using standard reconstruction methods and apparatus. The desired T2 contrast is produced primarily by the low-order views of each image and the high-order views enhance the structural details of each image. Accordingly, only the low-order views need be acquired separately for each image to provide the desired T2 contrast, and a single set of high order phase encoding views can be used to fill in the structure details in all of the images. However, this method provides a relatively small enhancement of the contrast unless a large number of high-order phase encoding views are acquired.

Another method of improving contrast is by adding contrast agents to the region of interest, such as administration of a paramagnetic contrast agent (for example, gadolinium) to blood vessels and creating the MRI images at a time when the concentration of contrast agent is at a maximum. This method is disclosed in U.S. Pat. No. 5,479,925A to Dumoulin et al., among others. The method is adapted to enhancing contrast in medical MRI but has limited utility in industrial application where there are no obvious sub-domains (such as blood vessels in medical MRI) into which to introduce the contrast agents and where the presence of a contrast agent in a finished product may well be undesirable.

US Patent Application US2004169512A to Jara discloses a method of combining three image-post-processing phases for the purpose of generating high-quality quantitative MR images (proton density (PD), T1, and T2) as well as high-quality virtual MR images with continuously adjustable computer-synthesized contrast weightings, from source images acquired directly with an MRI scanner. Each of the image-post-processing phases uses one or several new computer algorithms that improve image quality with respect to prior art, including linear-combination-of source-images (LCSI) algorithms for generating PD images and model-conforming algorithms for generating Q-MR images of tissue properties that influence NMR relaxation. However, the method depends on the presence of materials with different relaxation times in different parts of the scan (such as white matter and cerebrospinal fluid) to enable the enhanced contrast.

It is therefore a long felt need to provide an MRI device which provides high-contrast and high-resolution images especially for detecting contaminating or hazardous particles.

SUMMARY OF THE INVENTION

It is an object of the present invention to disclose an MRI-based hazard screening system, an explosive, narcotics or hazardous material detecting system, a walk through detector gate for higher throughput and the such (herein after 'hazard screening system'), detecting contaminating particles within or on the surface of an object, the system characterized by a sampling environment adapted for at least partially confining the object; the sampling environment is in fluid communication with at least one inlet and at least one fluid outlet; a fluid streamer for streaming a fluid, throughout the at least one inlet, towards the sampling environment where the fluid effectively interfaces the object; and further throughout the at least one outlet; and an MRI device in fluid communication with the at least one outlet, adapted for providing an image of the particles streamed by the fluid thereby screening the presence of the particles within or on the surface of the object.

It is another object of the present invention to disclose the MRI-based hazard screening system, wherein a separator and/or a collector is in fluid communication with the at least one outlet, the separator and/or collector is adapted for one or more of the following: (i) separating out particles carried downstream by the fluid stream, and (ii) collecting the particles in a predefined volume of interest.

It is another object of the present invention to disclose the MRI-based hazard screening system, wherein the MRI images the particles collected and accumulated in the volume of interest.

It is another object of the present invention to disclose the MRI-based hazard screening system, wherein the separator is facilitated by means of a cyclone or filter or both.

It is another object of the present invention to disclose the MRI-based hazard screening system, wherein the collector is facilitated by a particle collecting means selected from a group consisting of activated carbon, a filter including air filter, water filter, paper filter, HEPA filter, microfilter, water filter, water curtain, other conventional filter, other collection device, and any combination thereof.

It is another object of the present invention to disclose the MRI-based hazard screening system, wherein the fluid streamer is adapted for streaming a fluid in either continuously or batch-wise manner.

It is another object of the present invention to disclose the MRI-based hazard screening system, wherein the MRI is provided for a high-resolution high-contrast imaging of the particles; the MRI assembles the following: at least one first magnet configured to provide a high magnetic field for generating multiple time-resolved one or more first images at high resolution of at least a portion of the fluid; a least one second magnet configured to provide a low magnetic field for generating multiple time-resolved one or more second images at high contrast of at least a portion of the fluid; wherein at least one image of the first images and at least one image of the second images being generated in a time no greater than approximately the time between two first images; and a CPU to process the images comprising a computer readable medium containing instructions for generating at least one third image superimposing at least one image of the first images with at least one image of the second images, whereby a high-contrast, high-resolution real-time continuous image of the fluid is obtained.

It is another object of the present invention to disclose the MRI-based hazard screening system, wherein the at least one first magnet is of 2 Tesla and lower.

It is another object of the present invention to disclose the MRI-based hazard screening system, wherein the at least one first magnet is of 2 Tesla and higher.

It is another object of the present invention to disclose the MRI-based hazard screening system, wherein the at least one first magnet is selected from a group consisting of permanent magnets, electromagnets, superconducting magnets, and any combination thereof.

It is another object of the present invention to disclose the MRI-based hazard screening system, wherein the at least one second magnet is of 2 Tesla and lower.

It is another object of the present invention to disclose the MRI-based hazard screening system, wherein the at least one second magnet is of 2 Tesla and higher.

It is another object of the present invention to disclose the MRI-based hazard screening system, wherein the at least one second magnet is selected from a group consisting of permanent magnets, electromagnets, superconducting magnets, and any combination thereof.

It is another object of the present invention to disclose the MRI-based hazard screening system, wherein the at least one high magnetic field magnet is the at least one low magnetic field magnet.

It is another object of the present invention to disclose the MRI-based hazard screening system, wherein the angle between a perpendicular to the direction of flow and the high magnetic field is not the same as the angle between the perpendicular to the direction of flow and the low magnetic field.

It is another object of the present invention to disclose the MRI-based hazard screening system, wherein an integrated MRI device comprises both the high magnetic field magnets and the low magnetic field magnets.

It is another object of the present invention to disclose the MRI-based hazard screening system, wherein the MRI device comprises two MRI devices, one providing the high magnetic field magnets and one providing the low magnetic field magnets.

It is another object of the present invention to disclose the MRI-based hazard screening system, wherein the high magnetic field magnets have a duty cycle greater than approximately 50% and the low magnetic fields magnets have a duty cycle less than approximately 50%.

It is another object of the present invention to disclose the MRI-based hazard screening system, wherein at least one of the inlets or outlets is a member of a group consisting of a pipe, a duct, a tunnel, a conduit, a tube, a conveyor, a channel, a passage, and any combination thereof.

It is another object of the present invention to disclose the MRI-based hazard screening system, wherein the sampling environment is an integral part of the MRI device.

It is another object of the present invention to disclose the MRI-based hazard screening system, wherein the at least one outlet is an integral part of the MRI device.

It is another object of the present invention to disclose the MRI-based hazard screening system, wherein the fluid is at least one of a group consisting of a liquid, a gas, heated or cooled gas, mixture of two or more gases, ambient air, heated or cooled air, purified of filtered air, processed air, nitrogen, helium, oxygen, carbon dioxide, ozone, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combinations and mixtures thereof.

It is another object of the present invention to disclose the MRI-based hazard screening system, wherein either one of the following: the fluid or the object is a fluid process stream in a production process.

It is another object of the present invention to disclose the MRI-based hazard screening system, wherein the production process is in an industrial unit operation, the industrial unit operation a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI-based hazard screening system, wherein the fluid purification is purification of water.

It is another object of the present invention to disclose the MRI-based hazard screening system, wherein either one of the following: the fluid or the object is contained within a bypass stream from a production line.

It is another object of the present invention to disclose the MRI-based hazard screening system, wherein either one of the following: the fluid or the object is a fluid process stream within a batch process.

It is another object of the present invention to disclose the MRI-based hazard screening system, wherein either one of the following: the fluid or the object is flowing within an engine or combustion chamber.

It is another object of the present invention to disclose the MRI-based hazard screening system, wherein either one of the following: the fluid or the object is the effluent from the engine or combustion chamber.

It is another object of the present invention to disclose the MRI-based hazard screening system, wherein either one of the following: the fluid or the object is some fraction of the effluent from the engine or combustion chamber.

It is another object of the present invention to disclose the MRI-based hazard screening system, wherein either one of the following: the fluid or the object is used in fertility treatments.

It is another object of the present invention to disclose the MRI-based hazard screening system, wherein either one of the following: the fluid or the object is used for artificial insemination.

It is another object of the present invention to disclose the MRI-based hazard screening system, wherein either one of the following: the fluid or the object contains liposomes.

It is another object of the present invention to disclose the MRI-based hazard screening system, wherein either one of the following: the fluid or the object or the sampling environment is a part of an air curtain.

It is another object of the present invention to disclose the MRI-based hazard screening system, wherein either one of the following: the fluid or the object is a polymeric melt.

It is another object of the present invention to disclose the MRI-based hazard screening system, wherein the polymeric melt is a member of a group consisting of rubbers, polyesters, polyamides, polypropylenes, polyethylenes, polyurethanes, and any combination thereof.

It is another object of the present invention to disclose the MRI-based hazard screening system, wherein the system is a part of an integrated analysis and production system for a product.

It is another object of the present invention to disclose the MRI-based hazard screening system, wherein at least a part of the integrated analysis and production system complies with a NeSSI specification.

It is another object of the present invention to disclose the MRI-based hazard screening system, wherein at least a part of the integrated analysis and production system complies with ANSI/ISA SP76.00.2002 miniature, modular mechanical standard specifications.

It is another object of the present invention to disclose the MRI-based hazard screening system, wherein the either one of the following: the fluid or the object is a fluid within the body of a living subject.

It is another object of the present invention to disclose the MRI-based hazard screening system, wherein either one of the following: the fluid or the object flows from the body of a living subject, through the inlet and outlet, and is returned to the living subject It is another object of the present invention to disclose the MRI-based hazard screening system, adapted for imaging at least one first and at least one second image features; wherein the image processor is adapted to render the image by a Boolean method of correlating or combining the at least one first and at least one second image features.

It is another object of the present invention to disclose the MRI-based hazard screening system, wherein the Boolean method uses Boolean operators selected from the group consisting of OR, AND, NOT, EXCLUSIVE OR and any combination thereof.

It is another object of the present invention to disclose the MRI-based hazard screening system, wherein either one of the following: the fluid or the object is one of a group consisting of potable water, sewage, irrigation water, sea water, river water, lake water, industrial effluent, farm effluent, effluent from human habitation, road runoff, blood, lymph, organic and/or inorganic flowable matter, a row material or product thereof, an animal product or part thereof, a plant product or part thereof, a biological fluid, a biological tissue, a tissue extract, an industrial fluid, a flowing food sample, a beverage, wine, milk, ketchup, cleaning fluid, and any combination thereof.

It is another object of the present invention to disclose an MRI-based hazard screening method for detecting contaminating particles within or on the surface of an object, comprising providing a sampling environment for at least partially confining the object; the sampling environment is in fluid communication with at least one inlet and at least one fluid outlet; streaming a fluid, throughout the at least one inlet, towards the sampling environment where the fluid effectively interfaces the object; and further throughout the at least one outlet; providing an MRI device in fluid communication with the at least one outlet; and generating an image of the particles streamed by the fluid thereby screening for the presence of the particles within or on the surface of the object.

It is another object of the present invention to disclose the MRI-based hazard screening method, comprising an additional step of providing a separator and/or a collector in fluid communication with the at least one outlet.

It is another object of the present invention to disclose the MRI-based hazard screening method, comprising one or more of the following steps: (i) separating out particles carried downstream by the fluid stream, and (ii) collecting the particles in a predefined volume of interest.

It is another object of the present invention to disclose the MRI-based hazard screening method, comprising an additional step of imaging the particles collected and accumulated in the volume of interest.

It is another object of the present invention to disclose the MRI-based hazard screening method, comprising an additional step of facilitating the step of separating by means of a cyclone or filter or both.

It is another object of the present invention to disclose the MRI-based hazard screening method, comprising an additional step of facilitating the step of collecting by a particle collecting means selected from a group consisting of activated carbon, a filter including air filter, water filter, paper filter, HEPA filter, microfilter, water filter, water curtain, other conventional filter, other collection device, and any combination thereof.

It is another object of the present invention to disclose the MRI-based hazard screening method, comprising an additional step of streaming the fluid in either a continuous or a batch-wise manner.

It is another object of the present invention to disclose the MRI-based hazard screening method, comprising an additional step of providing a high-resolution high-contrast imaging of the particles; the step is carried out by the following steps: providing a least one first magnet configured to provide a high magnetic field for generating multiple time-resolved one or more first images at high resolution of at least a portion of the fluid; providing at least one second magnet configured to provide a low magnetic field for generating multiple time-resolved one or more second images at high contrast of at least portion of same the fluid; wherein at least one image of the first images and at least one image of the second images being generated in a time no greater than approximately the time between two first images; providing a CPU to process the images comprising a computer readable medium containing instructions for generating at least one third image superimposing at least one image of the first images with at least one image of the second images; generating multiple time resolved one or more first images at high resolution of at least a portion of the fluid; generating multiple time resolved one or more second images at high contrast of at least portion of the fluid; and superimposing at least one image of the first images with at least one image of the second images; whereby a high-contrast, high resolution real-time continuous image of the particles streamed by the fluid is obtained.

It is another object of the present invention to disclose the MRI-based hazard screening method, comprising an additional step of selecting the at least one first magnet to be of 2 Tesla and lower.

It is another object of the present invention to disclose the MRI-based hazard screening method, comprising an additional step of selecting the at least one first magnet to be of 2 Tesla and higher.

It is another object of the present invention to disclose the MRI-based hazard screening method, comprising an additional step of selecting the at least one first magnet from a group consisting of permanent magnets, electromagnets, superconducting magnets, and any combination thereof.

It is another object of the present invention to disclose the MRI-based hazard screening method, comprising an additional step of selecting the at least one second magnet to be of 2 Tesla and lower.

It is another object of the present invention to disclose the MRI-based hazard screening method, comprising an additional step of selecting the at least one second magnet to be of 2 Tesla and higher.

It is another object of the present invention to disclose the MRI-based hazard screening method, comprising an additional step of selecting the at least one second magnet from a group consisting of permanent magnets, electromagnets, superconducting magnets, and any combination thereof.

It is another object of the present invention to disclose the MRI-based hazard screening method, comprising an additional step of providing the at least one first magnet and the at least one second magnet as a single at least one magnet.

It is another object of the present invention to disclose the MRI-based hazard screening method, comprising an additional step of having the angle between a perpendicular to the direction of flow and the high magnetic field not the same as the angle between the perpendicular to the direction of flow and the low magnetic field.

It is another object of the present invention to disclose the MRI-based hazard screening method, comprising an additional step of selecting an integrated MRI device comprising both the high magnetic field magnets and the low magnetic field magnets.

It is another object of the present invention to disclose the MRI-based hazard screening method, comprising an additional step of selecting the MRI device comprising two MRI devices, one providing the high magnetic field magnets and one providing the low magnetic field magnets.

It is another object of the present invention to disclose the MRI-based hazard screening method, comprising an additional step of selecting a duty cycle for the high magnetic field magnets greater than approximately 50% and the low magnetic fields magnets have a duty cycle less than approximately 50%.

It is another object of the present invention to disclose the MRI-based hazard screening method, comprising an additional step of selecting the at least one of the inlets or outlets from a member of a group consisting of a pipe, a duct, a tunnel, a conduit, a tube, a conveyor, a channel, a passage, and any combination thereof.

It is another object of the present invention to disclose the MRI-based hazard screening method, comprising an additional step of providing the sampling environment as an integral part of the MRI device.

It is another object of the present invention to disclose the MRI-based hazard screening method, comprising an additional step of forming the at least one outlet as an integral part of the MRI device.

It is another object of the present invention to disclose the MRI-based hazard screening method, comprising an additional step of selecting the fluid from a group consisting of a liquid, a gas, heated or cooled gas, mixture of two or more gases, ambient air, heated or cooled air, purified of filtered air, processed air, nitrogen, helium, oxygen, carbon dioxide, ozone, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combinations and mixtures thereof.

It is another object of the present invention to disclose the MRI-based hazard screening method, comprising an additional step of providing either one of the following: the fluid or the object within a fluid process stream in a production process.

It is another object of the present invention to disclose the MRI-based hazard screening method, comprising an additional step of selecting the production process in an industrial unit operation, the industrial unit operation a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI-based hazard screening method, comprising an additional step of selecting water as the fluid purified in the fluid purification.

It is another object of the present invention to disclose the MRI-based hazard screening method, comprising an additional step of providing either one of the following: the fluid or the object contained within a bypass stream of a production line.

It is another object of the present invention to disclose the MRI-based hazard screening method, comprising an additional step of providing either one of the following: the fluid or the object in a fluid process stream within a batch process.

It is another object of the present invention to disclose the MRI-based hazard screening method, comprising an additional step of providing either one of the following: the fluid or the object within an engine or combustion chamber.

It is another object of the present invention to disclose the MRI-based hazard screening method, comprising an additional step of providing either one of the following: the fluid or the object as the effluent from the engine or combustion chamber.

It is another object of the present invention to disclose the MRI-based hazard screening method, comprising an additional step of providing either one of the following: the fluid or the object as some fraction of the effluent from the engine or combustion chamber.

It is another object of the present invention to disclose the MRI-based hazard screening method, comprising an additional step of selecting either one of the following: the fluid or the object as a fluid used in fertility treatments.

It is another object of the present invention to disclose the MRI-based hazard screening method, comprising an additional step of selecting either one of the following: the fluid or the object as a fluid used for artificial insemination.

It is another object of the present invention to disclose the MRI-based hazard screening method, comprising an additional step of selecting either one of the following: the fluid or the object as containing liposomes.

It is another object of the present invention to disclose the MRI-based hazard screening method, comprising an additional step of selecting either one of the following: the fluid or the object or the sampling environment as a part of an air curtain.

It is another object of the present invention to disclose the MRI-based hazard screening method, comprising an additional step of selecting either one of the following: the fluid or the object as a polymeric melt.

It is another object of the present invention to disclose the MRI-based hazard screening method, comprising an additional step of selecting the polymeric melt as a member of a group consisting of rubbers, polyesters, polyamides, polypropylenes, polyethylenes, polyurethanes, and any combination thereof.

It is another object of the present invention to disclose the MRI-based hazard screening method, comprising an additional step of integrating analysis and production of a product.

It is another object of the present invention to disclose the MRI-based hazard screening method, wherein at least a part of the step of integrating analysis and production of a product complies with a NeSSI specification.

It is another object of the present invention to disclose the MRI-based hazard screening method, wherein at least a part of the step of integrating analysis and production of a product complies with ANSI/ISA SP76.00.2002 miniature, modular mechanical standard specifications.

It is another object of the present invention to disclose the MRI-based hazard screening method, comprising an additional step of selecting either one of the following: the fluid or the object as a fluid within the body of a living subject.

It is another object of the present invention to disclose the MRI-based hazard screening method, comprising an additional step of passing either one of the following: the fluid or the object from the body of a living subject, through the inlet and outlet, and returning it to the living subject It is another object of the present invention to disclose the MRI-based hazard screening method, for imaging at least one first and at least one second image features; comprising an additional step of adapting the image processor to render the image by a Boolean method of correlating or combining the at least one first and at least one second image features.

It is another object of the present invention to disclose the MRI-based hazard screening method, comprising an additional step of selecting the Boolean operators of the Boolean method from the group consisting of OR, AND, NOT, EXCLUSIVE OR and any combination thereof.

It is another object of the present invention to disclose the MRI-based hazard screening method, comprising an additional step of selecting either one of the following: the fluid or the object from a group consisting of potable water, sewage, irrigation water, sea water, river water, lake water, industrial effluent, farm effluent, effluent from human habitation, road runoff, blood, lymph, organic and/or inorganic flowable matter, a row material or product thereof, an animal product or part thereof, a plant product or part thereof, a biological fluid, a biological tissue, a tissue extract, an industrial fluid, a flowing food sample, a beverage, wine, milk, ketchup, cleaning fluid, and any combination thereof.

It is another object of the present invention to disclose the MRI-based method, additionally comprising a step of indicating the type of the contaminating particles within or on the surface of the object.

BRIEF DESCRIPTION OF THE FIGURES

In order to better understand the invention and its implementation in practice, a plurality of embodiments will now be described, by way of non-limiting example only, with reference to the accompanying drawings, wherein FIGS. 1A, 1B, 1C and 1D depict MRI images of a cross sectional slice of a cucumber typically generated by the low intensity magnetic field device at different in-slice pixel sizes, respectively, in accordance with an embodiment of the present invention;

DETAILED DESCRIPTION OF THE PREFERRED EMBODIMENTS

Figure 2A:
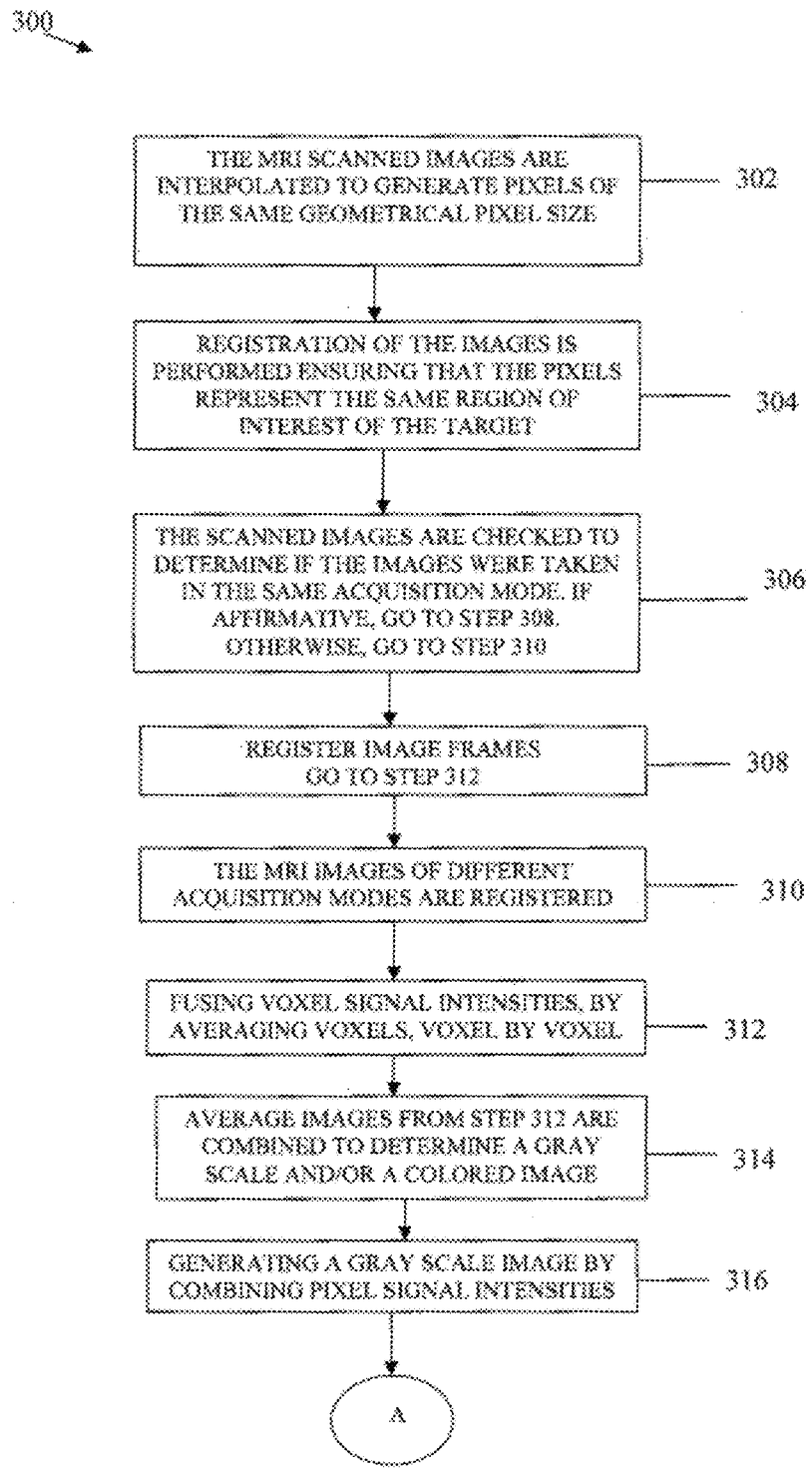
FIGS. 2A and 2B present flow charts of a typical procedure for fusing multiple sets of images of a given volume of the target into a single enhanced image, in accordance with an embodiment of the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing superimposed high resolution high contrast MRI images for detecting contaminating particles within or on the surface of an object.

As used herein, the term 'plurality' refers in a non-limiting manner to any integer equal to or greater than 1.

The term 'about' refers herein a value being ±25% of the defined measure.

The term 'approximately' refers herein a value being ±25% of the defined measure.

The term 'rapidly' refers herein to a time interval of less than 5 minutes.

The term 'nearly contemporaneously' refers to a time interval less than the time interval between generation of successive first images.

The term 'duty cycle' refers to the fraction of time during which a device is operated.

The term 'fluid' used herein refers in a non-limiting manner to a liquid, a gas, a solid phase and mixtures thereof, a slurry, a liquid containing particles, a gas containing particles, a gel, a sol, a suspension, a solution, a dispersion, a colloid, a mixture, an emulsion, an aerosol, a liquid containing solid particles, a gas containing solid particles and any combination thereof.

The term 'object' used herein refers in a non-limiting manner to a passenger, a man, animal, object, goods, enveloped cases and containers, a liquid, a gas, a solid phase and mixtures thereof, a slurry, a liquid containing particles, a gas containing particles, a gel, a sol, a suspension, a solution, a dispersion, a colloid, a mixture, an emulsion, an aerosol, a liquid containing solid particles, a gas containing solid particles, organic and/or inorganic flowable matter, a row material or product thereof, an animal product or part thereof, a plant product or part thereof, a biological fluid, a biological tissue, a tissue extract, an industrial fluid, a flowing food sample, a beverage, wine, milk, ketchup, water and any combination thereof and any otherwise semi batched, batched or continuous flowing media that can be continuously imaged.

According to certain embodiments, the biological fluid can be selected from a group comprising urine, blood, plasma, cerebrospinal fluid, saliva, amniotic fluid, bile and tears.

The term 'fluid streamer' refers herein after in a non limiting manner to any fluid moving machinery such as a machine for converting mechanical energy into fluid flow such as turbines and pumps, an engine e.g a combustion engine or a steam engine, compressors or fan, positive displacement machines, rotodynamic machines and any combination thereof.

The term 'contaminating particle' or 'contaminating particles' used herein refers in a non-limiting manner to hazardous biological or chemical residue which may includes a biological molecule, a chemical molecule, an analyte, a contaminant, a pathogen, a particle or any combination thereof. More specifically, it is within the scope of the present invention that a hazardous biological or chemical residue refers in a non-limiting manner to a protein, a pathogen or part thereof, a prion or part thereof, a virus or part thereof, a bacteria or part thereof, an organic or inorganic contaminant, a pathological isoform, a biomarker, an allergen, a neurotransmitter, an antigenic determinant, an epitope, a cell marker, cell membrane marker or epitope, a membrane marker, an enzyme, an organic or inorganic chemical molecule, an organic or inorganic analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue or part thereof, and any combination thereof. According to certain embodiments, the inorganic analyte may refer to molecular oxygen, oxygen-containing radicals, Antimony, Arsenic, Asbestos, Barium, Beryllium, Cadmium, Chromium, Cyanide, Fluoride, Mercury, Nickel, Nitrate, Nitrite, Selenium, Sodium, Thallium and any combination thereof.

It is also within the scope of the present invention that at least one property of said contaminating particle or hazardous biological or chemical residue is detected or analyzed by the high resolution high contrast MRI system and method as disclosed herein. Such a property may include, in a non-limiting manner a concentration, type or species, permeability, oxidation state, redox characteristic (reduction-oxidation state), activation state and any combination thereof.

The term 'paramagnetic agent' or 'paramagnetic core' used herein refers hereinafter in a non-limiting manner to a paramagnetic entity or agent or payload or species that may include a metal ion, a metal complex, oxides of a metal ion, oxides of a transition metal, mixed oxides of a transition metal, metal complexes, aggregates of metal complexes, polymer-bound metal complexes, stable organic radicals and their mixtures. Examples of metal ion may comprise an ion of nickel, iron, manganese, copper, gadolinium, europium and mixtures thereof. In a specific embodiment of the invention, the paramagnetic core constitutes a non ferrous oxide metal ion.

According to one embodiment the fluid is provided with liposomes loaded with a plurality of paramagnetic payloads.

It is thus according to one embodiment of the invention wherein an MRI-based hazard screening system for detecting contaminating particles within or on the surface of an object is disclosed. The system is preferably characterized by (a) a sampling environment adapted for at least partially confining the object; the sampling environment is in fluid communication with at least one inlet and at least one fluid outlet; (b) a fluid streamer for streaming a fluid, throughout the at least one inlet, towards the sampling environment where the fluid effectively interfaces the object; and further throughout the at least one outlet; and (c) an MRI device in fluid communication with the at least one outlet, adapted for providing an image of the particles streamed by the fluid thereby screening the presence of the particles within or on the surface of the object.

It is a main aspect of the invention that the object suspected to carry the contaminating particles may be a liquid, a gas, a solid phase and mixtures thereof.

According to another embodiment, the MRI-based hazard screening system further comprises a separator and/or a collector in fluid communication with the at least one outlet, the separator and/or collector is adapted for one or more of the following: (i) separating out particles carried downstream by the fluid stream, and (ii) collecting the particles in a predefined volume of interest.

According to a further embodiment, the MRI of the MRI-based hazard screening system as described above, images the particles collected and accumulated in the volume of interest.

According to a further embodiment, the fluid streamer is adapted for streaming a fluid in either continuously or batch-wise manner.

According to a further embodiment, the MRI of the MRI-based hazard screening system is provided for a high-resolution high-contrast imaging of the particles; the MRI assembles the following: (a) at least one first magnet configured to provide a high magnetic field for generating multiple time-resolved one or more first images at high resolution of at least a portion of the fluid; (b) a least one second magnet configured to provide a low magnetic field for generating multiple time-resolved one or more second images at high contrast of at least a portion of the fluid; wherein at least one image of the first images and at least one image of the second images being generated in a time no greater than approximately the time between two first images; and (c) a CPU to process the images comprising a computer readable medium containing instructions for generating at least one third image superimposing at least one image of the first images with at least one image of the second images, whereby a high-contrast, high-resolution real-time continuous image of the fluid is obtained.

Thus according to certain embodiments of the invention, superimposed MRI scanning systems are disclosed. Those systems comprise, inter alia, at least one high resolution MRI device, having means to scan high field, low contrast (HFLC) images, e.g., a commercially available 7 Tesla MRI device (hereinafter HFLC-MRI), and at least one low resolution MRI device, having means to scan low field, high contrast (LFHC) images, e.g., a commercially available Aspect Magnet Technologies Ltd. products (See company site at http://aspect-mr.com) 1 Tesla MRI device (hereinafter LFHC-MRI).

In another, preferred, embodiment of the system, the MRI images are generated continuously. Each HFLC image is followed by one or more LFHC images, so that the HFLC and LFHC images are nearly contemporaneous.

In preferred embodiments, high magnetic fields will be produced for a larger fraction of the operating time than low magnetic field will be. For non-limiting example, in an MRI-based device with separate magnets for producing HFLC images and for producing LFHC magnets, the fluid would be exposed to a high magnetic field for 90% of the time, while it would be exposed to a low magnetic field for only 10% of the time.

In another embodiment, the HFLC and LFHC images are generated concurrently, for at least part of their duty cycle.

It is according to yet another embodiment of the invention wherein MRI super-imposing scanning methods are disclosed. Those methods comprise, inter alia, steps of obtaining at least one high resolution high field, low contrast (HFLC) scan, e.g., by means of the aforesaid commercially available 7 Tesla MRI devices (hereinafter HFLC-images);

further obtaining at least one low resolution low field, high contrast LFHC scan (hereinafter LFHC-images), by means of e.g., one of the commercially available Aspect Magnet Technologies Ltd products 1 Tesla MRI devices (hereinafter LFHC-scans); and superimposing said at least one HFLC-images and said LFHC-images such that one or more superimposed high resolution high contrast images is obtained.

In another embodiment, a purpose-built device integrates both the high-field scanning system and the low-field scanning system. In such a purpose-built device, a single RF coil or RF probe can be used to measure the magnetic fields generating the HFLC and LFHC images, and only a single imaging chamber, CPU, etc. are needed.

Methods of superimposing the HFLC and LFHC scans include registering and aligning the images, also thresholding, region growing, and editing. Registering and aligning techniques include rendering the images using Boolean methods of correlating and combining the images. Combining binary images using Boolean logic makes it possible to select structures or objects based on multiple criteria, such as, but not limited to, masking and thresh-holding. The Boolean operators commonly used are OR, AND, NOT, EXCLUSIVE OR and combinations thereof.

Reference is now made to FIGS. 1A, 1B, 1C and 1D, which show MRI images of a cross sectional slice of a cucumber typically generated by the low intensity magnetic field device at different in-slice pixel sizes, respectively, in accordance with a preferred embodiment of the present invention;

FIG. 1A shows the cross section image of the cucumber 200 generated at an in-slice pixel size of 0.25 mm (high resolution) and a group of cucumber seeds 204 are clearly distinguishable from a cucumber background 202. However, due to the low SNR, the image of the cucumber seeds 204 is not clearly distinguishable from the cucumber background 202. A group of seeds 206 are not clearly distinguishable from the background 202. In addition, FIG. 1A shows a group of seeds 201 located on the periphery of the cucumber 200.

FIG. 1B shows a cross section image of the cucumber 1000 generated at an in-slice pixel size of 0.5 mm (medium resolution) and the group of seeds 1204 is clearly imaged. The image of the group of seeds 1206 is clearer. Due to edge effects, the border between the cucumber flesh 1202 and the group of cucumber seeds 1204 is not clearly defined. The group 206 is not clearly distinguishable from the cucumber background 202. Due to the decrease in the resolution, FIG. 1B does not clearly identify a group of seeds located on the periphery of the cucumber 1000.

FIG. 1C shows a cross section image of the cucumber 2000 generated at an in-slice pixel size of 1 mm (low resolution) and groups of cucumber seeds 2204 and 2206 are not clearly seen and the image is very blurred. Due to the further decrease in the resolution, FIG. 1C does not clearly identify a group of seeds located on the periphery of the cucumber 1000.

FIG. 1D shows a combined image 3000 of the high resolution (0.25 in-slice pixel size) and medium resolution (0.5 mm in-slice pixel size). The group of seeds 3214 is distinguishable from the cucumber background 3212 and the group of seeds 3216 is barely distinguishable from the cucumber background 3212. However, due to noise, the edges of the seeds 3214 and 3216 are not clearly discernible. FIG. 1D shows a group of seeds 3218 located on the periphery of the cucumber 3000. To summarize, the resolution in 3000 in FIG. 1D has the full resolution of cucumber 200 in FIG. 1A.

Figure 2B:
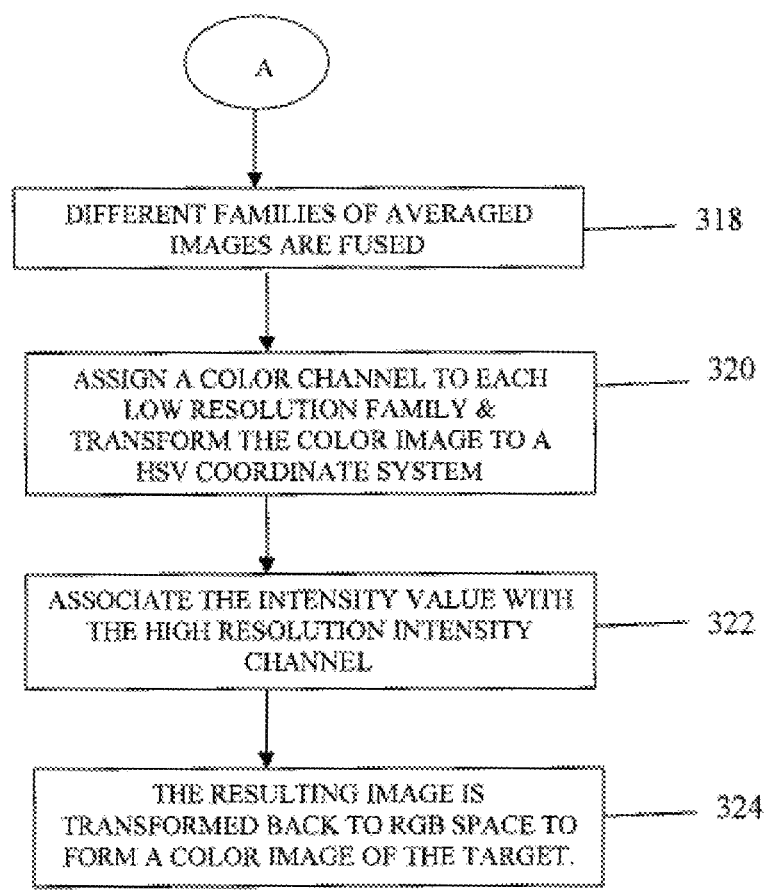

Reference is now made to FIGS. 2A and 2B which present flow charts of a typical procedure 300 for fusing multiple sets of images of a given volume into a single enhanced image, in accordance with a preferred embodiment of the present invention. The procedure 300 is controlled by a processing unit, wherein the images are taken at the same slice of a solid target.

In step 302, the MRI scanned images are interpolated in order to generate voxels of the same geometrical voxel size, as is known in the art.

In step 304, registration of the images acquired from the same acquisition mode is performed. The registration procedure ensures that the voxel representations of the images to be fused represent the same region of interest of the target.

In step 306, the scanned images are checked to determine if the images were taken in the same acquisition mode. If affirmative, go to step 308, otherwise go to step 310. In some embodiments of the invention, step 306 involves averaging the registered images to form a single image for each acquisition mode. This image includes a multiplicity of slices.

In step 308, the combined images from the distinct acquisition modes used to image the registered target. A typical registration method is "The Lukas-Kanade Optical Flow Method", as is known in art and described in "An Iterative Image Registration Technique with an Application to Stereo Vision", B. D. Lucas and T. Kanade (1981), published in the Proceedings of Imaging Understanding Workshop, pages 121-130. Since the distinct image acquisition modes may have a different appearance, other methods known in the art for registering multi-modality images may be used. These can be based on maximizing mutual information of images patches as is known in the art.

In step 310, registration of MR images of different acquisition modes is performed. In step 312, the registered MR images of different acquisition modes are fused according to any of the well known fusion methods. In the following steps of FIGS. 2A and 2B, a method that is suited to variable resolution images acquisitions is outlined:

In order to fuse the different acquisition modes of averaged images, the images are divided into two types: high resolution images and low resolution images. The high resolution images are combined to form a single monochrome image as follows:

The pixel values are combined using some weighting, which can be assigned by a variety of methods, such as a principal component analysis. Principal component analysis is known in the art and is described in "*Principal Component Analysis*", by I. T. Jolliffe, Series: Springer Series in Statistics, 2nd ed., Springer, N.Y., 2002, XXIX, 487 p. 28 illus. ISBN 978-0-387-95442-4. This combined monochrome image controls the brightness and/or intensity of the fused colored image while the low resolution images will control the spectral resolution of the fused image.

The steps for fusing these high resolution and low resolution images to form a colored image are further outlined in FIG. 2A and FIG. 2B.

In step 314, the averaged images from step 312 are combined to determine a gray scale and/or a colored image. In step 316, a gray scale image is generated by combining pixel signal intensities. In step 318, different families of averaged images are fused.

In step 320, each low-resolution image acquisition mode is assigned a color channel: for example, red, green and blue, for three acquisition modes. The low resolution image is transformed to the HSV (hue, saturation, value) basis.

In step 322, the intensity channel (value) is associated with the high resolution monochrome image and/or combined with the low-resolution intensity channel, for example by the Brovey method, as is known in the art.

In step 324, the resulting image is transformed back to RGB space to form a colored fused final image of the target.

Reference is now made to FIGS. 3A-3D, which compare the results of combining multi-resolution images, in accordance with a preferred embodiment of the present invention.

Figure 3B:
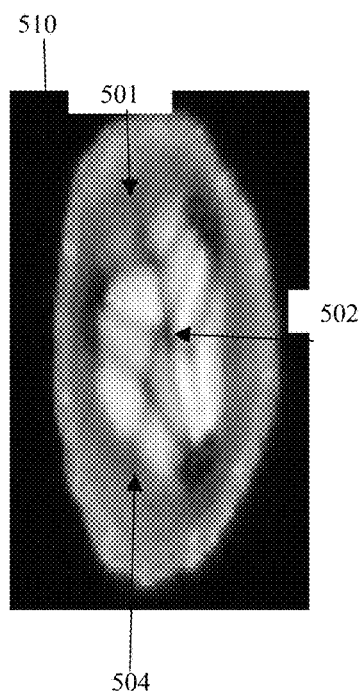
FIGS. 3A-3D compare the results of combining multi-resolutions images, in accordance with a preferred embodiment of the present invention.
Figure 3D:
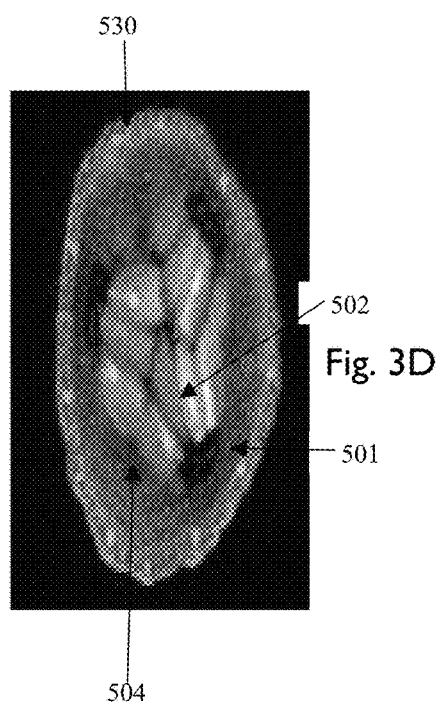
Figure 3A:
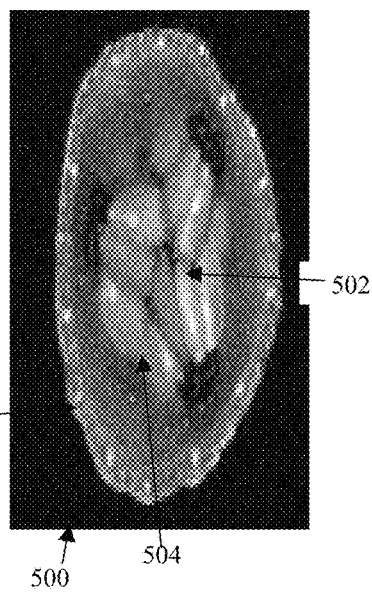

FIG. 3A shows a high resolution image 500 of a cross section of a cucumber 501 and groups of cucumber seeds 502 and 504. FIG. 3A is similar to the high resolution scan shown in FIG. 1A.

FIG. 3B shows a high resolution image 510 of a cross section of the cucumber 501 and groups of cucumber seeds 502 and 504. In the image 510, the high resolution image (FIG. 1A), the medium resolution image (FIG. 1B) and the low resolution image (FIG. 1C) are combined by a IHS method as described in "Application of the IHS Color Transform to the Processing of Multisensor Data and Image Enhancement", (Haydn, R., Dalke, G. W. and Henkel, J.: Proc. of the International Symposium on Remote Sensing of Arid and Semiarid Lands, Cairo, pp. 599-616, 1982.), to form the high resolution, high contrast image shown in FIG. 3D. The high resolution image 520 is clearer than the colored image 510.

Figure 3C:
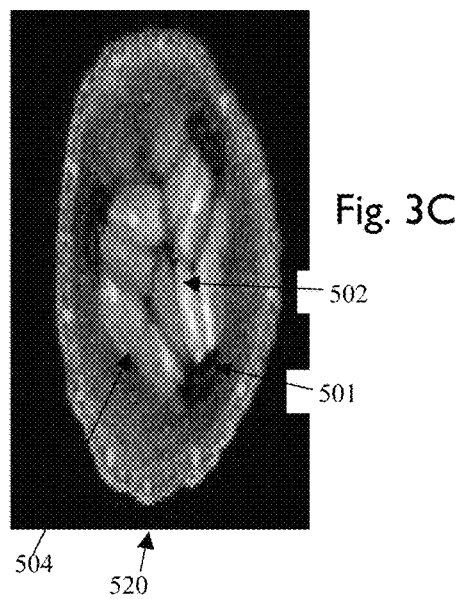

FIG. 3C shows a high resolution image 520 of a cross section of the cucumber 501 and groups of cucumber seeds 502 and 504. In the image 520, the high resolution image (FIG. 1A), the medium resolution image (FIG. 1B) and the low resolution image (FIG. 1C) are combined by the Brovey method, as is known in the art (step 314, FIG. 2A). The image 530 clearly distinguishes between the groups of cucumber seeds 502 and 504 and the groups of cucumber seeds 502 and 504 are clearly distinguishable from the cucumber background 501.

The present system can be used where the analyzed objects are selected from agricultural raw materials or products, preferably fluid products, cosmetics, chemicals, powders, gases, medicaments, industrial matters, or any other flowable combination of solid, liquid and gas.

In another embodiment of the present invention, the fluid is contained in a pipe or conduit which passes through the volume of the high magnetic field and the low magnetic field MRI scans.

Figure 4:
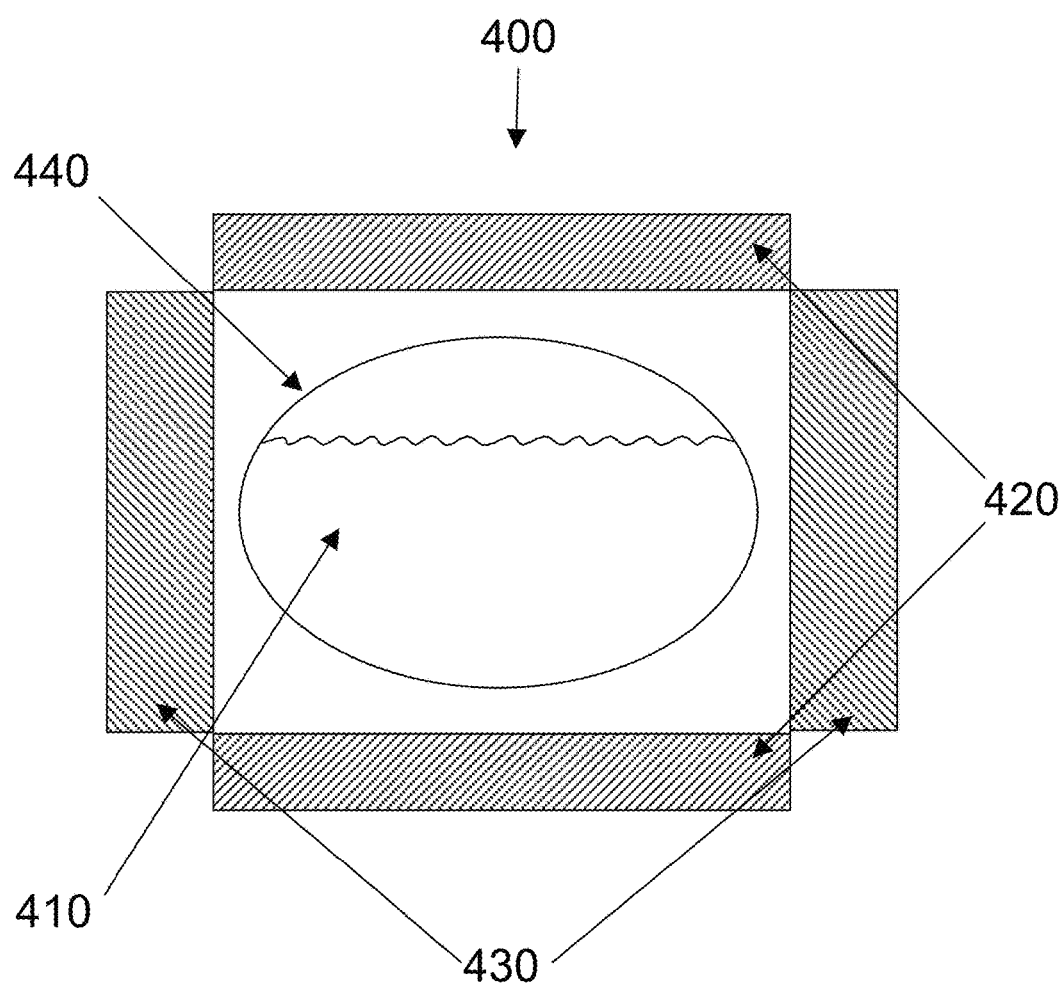
FIG. 4 schematically illustrates an embodiment with the envelope of magnets for the fluid part of an MRI device.

In another embodiment, the envelope for the fluid in the region of the volume of the high magnetic field and low-field MRI scans is the MRI itself. A non-limiting example of an embodiment of this type is schematically illustrated in FIG. 4. The device (400) comprises two sets of magnets (420, 430). The RF coils (not shown) are part of an envelope (440) which contains the fluid (410). In this embodiment, the high magnetic field magnets (420) are in a horizontal orientation, while the low magnetic field magnets (430) are in a vertical orientation. In other embodiments, the low field magnets can be inside the high magnetic field magnets. In yet other embodiments, the low magnetic field magnets can be outside the high magnetic field magnets.

In some embodiments, the two sets of magnets form part of a single, integrated device. In other embodiments, each set of magnets is part of a separate device, such as the commercially available devices described hereinabove.

Example 1

Use of the System and Method of the Present Invention for Screening Passengers Carrying Hazardous Biological or Chemical Agent Residues in Airports It is within the scope of the present invention to provide means and methods for screening passengers, for example in the airport, for hazardous biological or chemical agent residues they may be carrying. A non-limiting example of such an agent is a disease pathogen. Another non-limiting example is a nerve gas such as Sarin or explosive residue. Such a screening system and method may be applied in main junctions such as airports and public places.

According to one embodiment, the method and system for rapidly screening for the presence of hazardous biological or chemical agent residues, for example, a contagious disease-causing pathogen carried by an individual, can be used in homeland security. In one embodiment a sampling environment is provided for at least partially confining an object. According to certain embodiments, the object may be an individual or a material, particularly a followable material that is suspected of carrying a contaminating particle. According to a further embodiment, the sampling environment is in fluid communication with at least one inlet and at least one fluid outlet. In a preferred embodiment, fluid is streamed throughout the at least one inlet, towards the sampling environment such that the fluid effectively interfaces with the object; and further throughout the at least one outlet. The fluid is then streamed to an MRI device which is in fluid communication with the at least one outlet. The MRI device is capable of generating an image of the particles streamed by the fluid, thus screening for the presence of the particles within or on the surface of the suspected object.

In a specific embodiment, the MRI-based system of the present invention can be combined with a technique using particles such as liposomes configured to interact with a target biochemical molecule, each liposome comprising a paramagnetic core and a moiety configured to interact with a target biochemical molecule. This technique can fish out and detect biological or chemical agents such as pathogens and/or minuscule amounts of DNA or other residue, marker or particulate of a biological or chemical agent. The change in the magnetic signature measured by the MRI-based system of the present invention can be detected on a computer screen or portable electronic device, such as a smartphone, and determination be made whether the sample or object is infected with a particular pathogen or contains residues of a hazardous biological or chemical agent.

Figure 5:
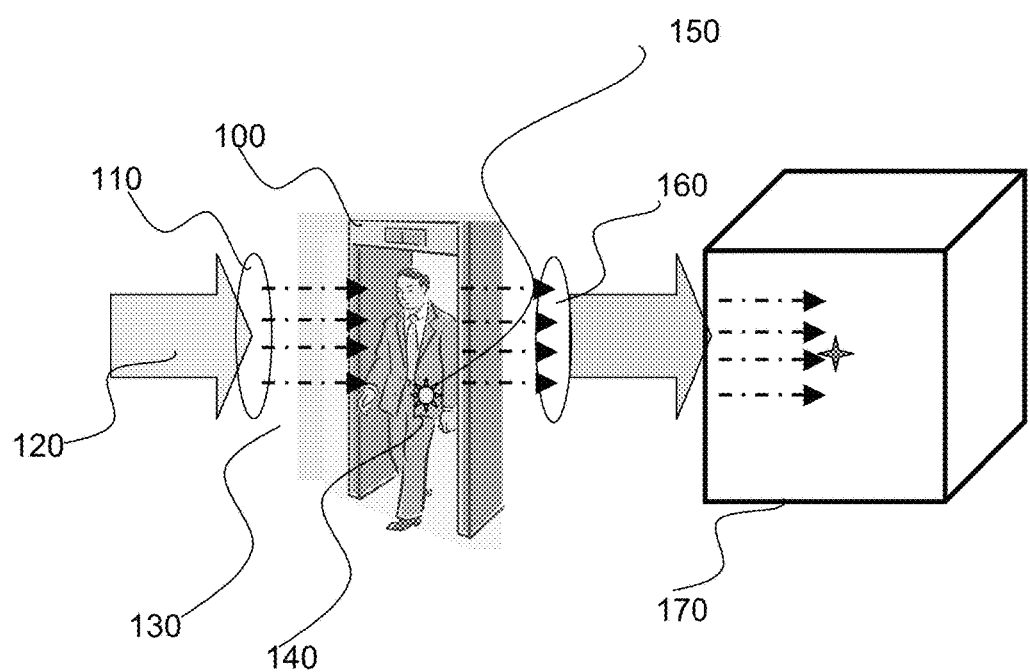
FIG. 5 schematically illustrates embodiments of a system and steps for rapidly screening for the presence of hazardous biological or chemical agent residues carried by an individual.

The method of the present invention can be used for screening passengers, for example in the airport, to determine if they are carrying (innocently or otherwise) residues of a hazardous biological or chemical agent, such as a contaminating disease-causing pathogen or particles thereof, and thereby prevent the spread of the disease before it becomes a pandemic. A typical test which may be applied in airports, for example, is schematically described in FIG. 5, showing the following embodiments and steps:

A passenger 140 suspected to carry a contaminating particle 150 is asked to pass through a sampling environment 100. The sampling environment is in fluid communication with at least one inlet 110 and at least one fluid outlet 160. As defined herein above, it is within the scope of the present invention that the term fluid may refer to a liquid, a gas, a solid phase and mixtures thereof, a slurry, a liquid containing particles, a gas containing particles, a gel, a sol, a suspension, a solution, a dispersion, a colloid, a mixture, an emulsion, an aerosol, a liquid containing solid particles, a gas containing solid particles and any combination thereof.

Fluid 120 is then streamed by means of a fluid streamer throughout said at least one inlet 110, towards said sampling environment 100 where said fluid 130 effectively interfaces the passenger 140 suspected to carry said contaminating particle 150; and further throughout said at least one outlet 160. According to a further embodiment, particles carried by the fluid stream 130 are then moved to an MRI device 170 which is in fluid communication with said at least one outlet 160. The MRI device of the present invention is preferably adapted for providing a high-contrast high-resolution real-time continuous image of the fluid and thus an image of the particles streamed by the fluid is obtained.

Figure 6:
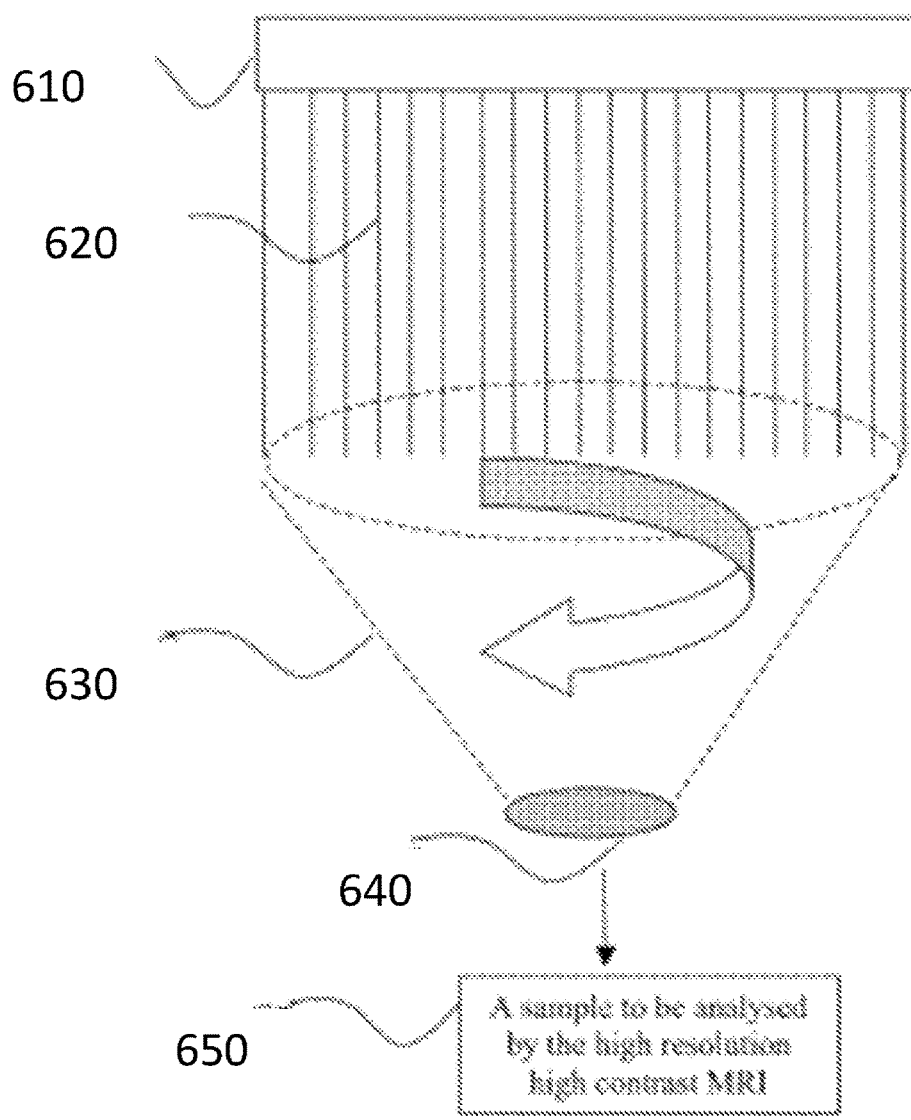
FIG. 6 schematically illustrates a specific configuration of the sampling environment, in accordance with an embodiment of the present invention.

FIG. 6 depicts a specific embodiment of the system and method of the present invention. A specific configuration of the sampling environment may be in a form where an air stream 620 is generated by an air curtain 610. As used herein the term 'air curtain' refers to a fan-powered device or the like. A common configuration for an air curtain is a downward-facing blower fan that blows air across a defined surface. The fan should be powerful enough to generate a jet of air that can reach the floor.

According to a further embodiment, particles carried by the air stream 620 are then separated downstream; using separation means, preferably using a cyclonic separation means 630. It is acknowledged that a cyclonic separation system is herein refers to a means for removing and/or collecting particles from an air, gas or liquid stream, through vortex separation. The rotational effects and gravity are used to separate mixtures of solids and fluids. The particles that are carried out by the air stream 620 may include pathogens and/or debris, residues or particles of a biological or chemical agent with which the passenger has been in recent contact.

According to a further embodiment, the particles carried on the separated downstream air are collected by a particle collecting means 640 (such as activated carbon, a filter, HEPA filter, microfilter, water filter, air filter or water curtain, or any other conventional filter or collection device) to obtain a sample for analysis 650. The sample containing the separated particles or residues 650 is then subjected to an MRI device configured to provide an image of the particles in the sample thereby screening the presence of said particles carried by an individual and the matter investigated further. In this embodiment, detection is accomplished in less than about a minute, as this is not an unacceptable time for passage of a passenger through a screening device. In a preferred embodiment, a high-contrast, high-resolution real-time continuous image of the sample is obtained using the MRI device of the present invention. Thus the present invention provides a system and method to image such contaminating and hazardous particles and to enable the detection of the presence of small amounts of hazardous biological or chemical agent residues within or in the surface of an object, including a human individual.

Example 2

Use of the System and Method of the Present Invention for Screening Contaminating Particles in Portable Water or Flowing Media According to this embodiment, a fluid, or flowing media such as potable water in a national or local water carrier system, can be screened for contaminating particles such as small amounts of a hazardous biological or chemical agent. In this embodiment, the water is continuously sampled, with analyzable samples flowing through the MRI-based device of the present invention. If there are hazardous biological or chemical agents present, they are detected by the high-contrast, high-resolution MRI device by a real-time and continuous imaging manner of the sample. In this embodiment, it is feasible for detection to take several minutes.

Thus according to a certain aspect of the invention, an MRI-based system and method for rapidly screening for contaminating particles such as hazardous biological or chemical residue in a flowing main fluid is disclosed. The aforementioned system comprising: an MRI device as disclosed herein above; a main fluid; a purging device to separate an analyzable-size sample of fluid from said main fluid, said separator fluidly connected to said MRI device; a facilitator to facilitate flow of said analyzable-size sample through said MRI device; whereby a high-contrast, high-resolution real-time continuous image of said at least one analyzable-size sample of said fluid is obtained, and further whereby the presence of said hazardous biological or chemical agent residues in said main fluid is indicated.

It a main object of the present invention to disclose an MRI-based hazard screening system for detecting contaminating particles within or on the surface of an object, the system characterized by a sampling environment adapted for at least partially confining the object; the sampling environment is in fluid communication with at least one inlet and at least one fluid outlet; a fluid streamer for streaming a fluid, throughout the at least one inlet, towards the sampling environment where the fluid effectively interfaces the object; and further throughout the at least one outlet; and an MRI device in fluid communication with the at least one outlet, adapted for providing an image of the particles streamed by the fluid thereby screening the presence of the particles within or on the surface of the object.

It is another object of the present invention to disclose the MRI-based hazard screening system, wherein a separator and/or a collector is in fluid communication with the at least one outlet, the separator and/or collector is adapted for one or more of the following: (i) separating out particles carried downstream by the fluid stream, and (ii) collecting the particles in a predefined volume of interest.

It is another object of the present invention to disclose the MRI-based hazard screening system, wherein the MRI images the particles collected and accumulated in the volume of interest.

It is another object of the present invention to disclose the MRI-based hazard screening system, wherein the separator is facilitated by means of a cyclone or filter or both.

It is another object of the present invention to disclose the MRI-based hazard screening system, wherein the collector is facilitated by a particle collecting means selected from a group consisting of activated carbon, a filter including air filter, water filter, paper filter, HEPA filter, microfilter, water filter, water curtain, other conventional filter, other collection device, and any combination thereof.

It is another object of the present invention to disclose the MRI-based hazard screening system, wherein the fluid streamer is adapted for streaming a fluid in either continuously or batch-wise manner.

It is another object of the present invention to disclose the MRI-based hazard screening system, wherein the MRI is provided for a high-resolution high-contrast imaging of the particles; the MRI assembles the following: at least one first magnet configured to provide a high magnetic field for generating multiple time-resolved one or more first images at high resolution of at least a portion of the fluid; a least one second magnet configured to provide a low magnetic field for generating multiple time-resolved one or more second images at high contrast of at least a portion of the fluid; wherein at least one image of the first images and at least one image of the second images being generated in a time no greater than approximately the time between two first images; and a CPU to process the images comprising a computer readable medium containing instructions for generating at least one third image superimposing at least one image of the first images with at least one image of the second images, whereby a high-contrast, high-resolution real-time continuous image of the fluid is obtained.

It is another object of the present invention to disclose the MRI-based hazard screening system, wherein the at least one first magnet is of 2 Tesla and lower.

It is another object of the present invention to disclose the MRI-based hazard screening system, wherein the at least one first magnet is of 2 Tesla and higher.

It is another object of the present invention to disclose the MRI-based hazard screening system, wherein the at least one first magnet is selected from a group consisting of permanent magnets, electromagnets, superconducting magnets, and any combination thereof.

It is another object of the present invention to disclose the MRI-based hazard screening system, wherein the at least one second magnet is of 2 Tesla and lower.

It is another object of the present invention to disclose the MRI-based hazard screening system, wherein the at least one second magnet is of 2 Tesla and higher.

It is another object of the present invention to disclose the MRI-based hazard screening system, wherein the at least one second magnet is selected from a group consisting of permanent magnets, electromagnets, superconducting magnets, and any combination thereof.

It is another object of the present invention to disclose the MRI-based hazard screening system, wherein the at least one high magnetic field magnet is the at least one low magnetic field magnet.

It is another object of the present invention to disclose the MRI-based hazard screening system, wherein the angle between a perpendicular to the direction of flow and the high magnetic field is not the same as the angle between the perpendicular to the direction of flow and the low magnetic field.

It is another object of the present invention to disclose the MRI-based hazard screening system, wherein an integrated MRI device comprises both the high magnetic field magnets and the low magnetic field magnets.

It is another object of the present invention to disclose the MRI-based hazard screening system, wherein the MRI device comprises two MRI devices, one providing the high magnetic field magnets and one providing the low magnetic field magnets.

It is another object of the present invention to disclose the MRI-based hazard screening system, wherein the high magnetic field magnets have a duty cycle greater than approximately 50% and the low magnetic fields magnets have a duty cycle less than approximately 50%.

It is another object of the present invention to disclose the MRI-based hazard screening system, wherein at least one of the inlets or outlets is a member of a group consisting of a pipe, a duct, a tunnel, a conduit, a tube, a conveyor, a channel, a passage, and any combination thereof.

It is another object of the present invention to disclose the MRI-based hazard screening system, wherein the sampling environment is an integral part of the MRI device.

It is another object of the present invention to disclose the MRI-based hazard screening system, wherein the at least one outlet is an integral part of the MRI device.

It is another object of the present invention to disclose the MRI-based hazard screening system, wherein the fluid is at least one of a group consisting of a liquid, a gas, heated or cooled gas, mixture of two or more gases, ambient air, heated or cooled air, purified of filtered air, processed air, nitrogen, helium, oxygen, carbon dioxide, ozone, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combinations and mixtures thereof.

It is another object of the present invention to disclose the MRI-based hazard screening system, wherein either one of the following: the fluid or the object is a fluid process stream in a production process.

It is another object of the present invention to disclose the MRI-based hazard screening system, wherein the production process is in an industrial unit operation, the industrial unit operation a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI-based hazard screening system, wherein the fluid purification is purification of water.

It is another object of the present invention to disclose the MRI-based hazard screening system, wherein either one of the following: the fluid or the object is contained within a bypass stream from a production line.

It is another object of the present invention to disclose the MRI-based hazard screening system, wherein either one of the following: the fluid or the object is a fluid process stream within a batch process.

It is another object of the present invention to disclose the MRI-based hazard screening system, wherein either one of the following: the fluid or the object is flowing within an engine or combustion chamber.

It is another object of the present invention to disclose the MRI-based hazard screening system, wherein either one of the following: the fluid or the object is the effluent from the engine or combustion chamber.

It is another object of the present invention to disclose the MRI-based hazard screening system, wherein either one of the following: the fluid or the object is some fraction of the effluent from the engine or combustion chamber.

It is another object of the present invention to disclose the MRI-based hazard screening system, wherein either one of the following: the fluid or the object is used in fertility treatments.

It is another object of the present invention to disclose the MRI-based hazard screening system, wherein either one of the following: the fluid or the object is used for artificial insemination.

It is another object of the present invention to disclose the MRI-based hazard screening system, wherein either one of the following: the fluid or the object contains liposomes.

It is another object of the present invention to disclose the MRI-based hazard screening system, wherein either one of the following: the fluid or the object or the sampling environment is a part of an air curtain.

It is another object of the present invention to disclose the MRI-based hazard screening system, wherein either one of the following: the fluid or the object is a polymeric melt.

It is another object of the present invention to disclose the MRI-based hazard screening system, wherein the polymeric melt is a member of a group consisting of rubbers, polyesters, polyamides, polypropylenes, polyethylenes, polyurethanes, and any combination thereof.

It is another object of the present invention to disclose the MRI-based hazard screening system, wherein the system is a part of an integrated analysis and production system for a product.

It is another object of the present invention to disclose the MRI-based hazard screening system, wherein at least a part of the integrated analysis and production system complies with a NeSSI specification.

It is another object of the present invention to disclose the MRI-based hazard screening system, wherein at least a part of the integrated analysis and production system complies with ANSI/ISA SP76.00.2002 miniature, modular mechanical standard specifications.

It is another object of the present invention to disclose the MRI-based hazard screening system, wherein the either one of the following: the fluid or the object is a fluid within the body of a living subject.

It is another object of the present invention to disclose the MRI-based hazard screening system, wherein either one of the following: the fluid or the object flows from the body of a living subject, through the inlet and outlet, and is returned to the living subject It is another object of the present invention to disclose the MRI-based hazard screening system, adapted for imaging at least one first and at least one second image features; wherein the image processor is adapted to render the image by a Boolean method of correlating or combining the at least one first and at least one second image features.

It is another object of the present invention to disclose the MRI-based hazard screening system, wherein the Boolean method uses Boolean operators selected from the group consisting of OR, AND, NOT, EXCLUSIVE OR and any combination thereof.

It is another object of the present invention to disclose the MRI-based hazard screening system, wherein either one of the following: the fluid or the object is one of a group consisting of potable water, sewage, irrigation water, sea water, river water, lake water, industrial effluent, farm effluent, effluent from human habitation, road runoff, blood, lymph, organic and/or inorganic flowable matter, a row material or product thereof, an animal product or part thereof, a plant product or part thereof, a biological fluid, a biological tissue, a tissue extract, an industrial fluid, a flowing food sample, a beverage, wine, milk, ketchup, cleaning fluid, and any combination thereof.

It is another object of the present invention to disclose an MRI-based hazard screening method for detecting contaminating particles within or on the surface of an object, comprising providing a sampling environment for at least partially confining the object; the sampling environment is in fluid communication with at least one inlet and at least one fluid outlet; streaming a fluid, throughout the at least one inlet, towards the sampling environment where the fluid effectively interfaces the object; and further throughout the at least one outlet; providing an MRI device in fluid communication with the at least one outlet; and generating an image of the particles streamed by the fluid thereby screening for the presence of the particles within or on the surface of the object.

It is another object of the present invention to disclose the MRI-based hazard screening method, comprising an additional step of providing a separator and/or a collector in fluid communication with the at least one outlet.

It is another object of the present invention to disclose the MRI-based hazard screening method, comprising one or more of the following steps: (i) separating out particles carried downstream by the fluid stream, and (ii) collecting the particles in a predefined volume of interest.

It is another object of the present invention to disclose the MRI-based hazard screening method, comprising an additional step of imaging the particles collected and accumulated in the volume of interest.

It is another object of the present invention to disclose the MRI-based hazard screening method, comprising an additional step of facilitating the step of separating by means of a cyclone or filter or both.

It is another object of the present invention to disclose the MRI-based hazard screening method, comprising an additional step of facilitating the step of collecting by a particle collecting means selected from a group consisting of activated carbon, a filter including air filter, water filter, paper filter, HEPA filter, microfilter, water filter, water curtain, other conventional filter, other collection device, and any combination thereof.

It is another object of the present invention to disclose the MRI-based hazard screening method, comprising an additional step of streaming the fluid in either a continuous or a batch-wise manner.

It is another object of the present invention to disclose the MRI-based hazard screening method, comprising an additional step of providing a high-resolution high-contrast imaging of the particles; the step is carried out by the following steps: providing a least one first magnet configured to provide a high magnetic field for generating multiple time-resolved one or more first images at high resolution of at least a portion of the fluid; providing at least one second magnet configured to provide a low magnetic field for generating multiple time-resolved one or more second images at high contrast of at least portion of same the fluid; wherein at least one image of the first images and at least one image of the second images being generated in a time no greater than approximately the time between two first images; providing a CPU to process the images comprising a computer readable medium containing instructions for generating at least one third image superimposing at least one image of the first images with at least one image of the second images; generating multiple time resolved one or more first images at high resolution of at least a portion of the fluid; generating multiple time resolved one or more second images at high contrast of at least portion of the fluid; and superimposing at least one image of the first images with at least one image of the second images; whereby a high-contrast, high resolution real-time continuous image of the particles streamed by the fluid is obtained.

It is another object of the present invention to disclose the MRI-based hazard screening method, comprising an additional step of selecting the at least one first magnet to be of 2 Tesla and lower.

It is another object of the present invention to disclose the MRI-based hazard screening method, comprising an additional step of selecting the at least one first magnet to be of 2 Tesla and higher.

It is another object of the present invention to disclose the MRI-based hazard screening method, comprising an additional step of selecting the at least one first magnet from a group consisting of permanent magnets, electromagnets, superconducting magnets, and any combination thereof.

It is another object of the present invention to disclose the MRI-based hazard screening method, comprising an additional step of selecting the at least one second magnet to be of 2 Tesla and lower.

It is another object of the present invention to disclose the MRI-based hazard screening method, comprising an additional step of selecting the at least one second magnet to be of 2 Tesla and higher.

It is another object of the present invention to disclose the MRI-based hazard screening method, comprising an additional step of selecting the at least one second magnet from a group consisting of permanent magnets, electromagnets, superconducting magnets, and any combination thereof.

It is another object of the present invention to disclose the MRI-based hazard screening method, comprising an additional step of providing the at least one first magnet and the at least one second magnet as a single at least one magnet.

It is another object of the present invention to disclose the MRI-based hazard screening method, comprising an additional step of having the angle between a perpendicular to the direction of flow and the high magnetic field not the same as the angle between the perpendicular to the direction of flow and the low magnetic field.

It is another object of the present invention to disclose the MRI-based hazard screening method, comprising an additional step of selecting an integrated MRI device comprising both the high magnetic field magnets and the low magnetic field magnets.

It is another object of the present invention to disclose the MRI-based hazard screening method, comprising an additional step of selecting the MRI device comprising two MRI devices, one providing the high magnetic field magnets and one providing the low magnetic field magnets.

It is another object of the present invention to disclose the MRI-based hazard screening method, comprising an additional step of selecting a duty cycle for the high magnetic field magnets greater than approximately 50% and the low magnetic fields magnets have a duty cycle less than approximately 50%.

It is another object of the present invention to disclose the MRI-based hazard screening method, comprising an additional step of selecting the at least one of the inlets or outlets from a member of a group consisting of a pipe, a duct, a tunnel, a conduit, a tube, a conveyor, a channel, a passage, and any combination thereof.

It is another object of the present invention to disclose the MRI-based hazard screening method, comprising an additional step of providing the sampling environment as an integral part of the MRI device.

It is another object of the present invention to disclose the MRI-based hazard screening method, comprising an additional step of forming the at least one outlet as an integral part of the MRI device.

It is another object of the present invention to disclose the MRI-based hazard screening method, comprising an additional step of selecting the fluid from a group consisting of a liquid, a gas, heated or cooled gas, mixture of two or more gases, ambient air, heated or cooled air, purified of filtered air, processed air, nitrogen, helium, oxygen, carbon dioxide, ozone, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combinations and mixtures thereof.

It is another object of the present invention to disclose the MRI-based hazard screening method, comprising an additional step of providing either one of the following: the fluid or the object within a fluid process stream in a production process.

It is another object of the present invention to disclose the MRI-based hazard screening method, comprising an additional step of selecting the production process in an industrial unit operation, the industrial unit operation a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI-based hazard screening method, comprising an additional step of selecting water as the fluid purified in the fluid purification.

It is another object of the present invention to disclose the MRI-based hazard screening method, comprising an additional step of providing either one of the following: the fluid or the object contained within a bypass stream of a production line.

It is another object of the present invention to disclose the MRI-based hazard screening method, comprising an additional step of providing either one of the following: the fluid or the object in a fluid process stream within a batch process.

It is another object of the present invention to disclose the MRI-based hazard screening method, comprising an additional step of providing either one of the following: the fluid or the object within an engine or combustion chamber.

It is another object of the present invention to disclose the MRI-based hazard screening method, comprising an additional step of providing either one of the following: the fluid or the object as the effluent from the engine or combustion chamber.

It is another object of the present invention to disclose the MRI-based hazard screening method, comprising an additional step of providing either one of the following: the fluid or the object as some fraction of the effluent from the engine or combustion chamber.

It is another object of the present invention to disclose the MRI-based hazard screening method, comprising an additional step of selecting either one of the following: the fluid or the object as a fluid used in fertility treatments.

It is another object of the present invention to disclose the MRI-based hazard screening method, comprising an additional step of selecting either one of the following: the fluid or the object as a fluid used for artificial insemination.

It is another object of the present invention to disclose the MRI-based hazard screening method, comprising an additional step of selecting either one of the following: the fluid or the object as containing liposomes.

It is another object of the present invention to disclose the MRI-based hazard screening method, comprising an additional step of selecting either one of the following: the fluid or the object or the sampling environment as a part of an air curtain.

It is another object of the present invention to disclose the MRI-based hazard screening method, comprising an additional step of selecting either one of the following: the fluid or the object as a polymeric melt.

It is another object of the present invention to disclose the MRI-based hazard screening method, comprising an additional step of selecting the polymeric melt as a member of a group consisting of rubbers, polyesters, polyamides, polypropylenes, polyethylenes, polyurethanes, and any combination thereof.

It is another object of the present invention to disclose the MRI-based hazard screening method, comprising an additional step of integrating analysis and production of a product.

It is another object of the present invention to disclose the MRI-based hazard screening method, wherein at least a part of the step of integrating analysis and production of a product complies with a NeSSI specification.

It is another object of the present invention to disclose the MRI-based hazard screening method, wherein at least a part of the step of integrating analysis and production of a product complies with ANSI/ISA SP76.00.2002 miniature, modular mechanical standard specifications.

It is another object of the present invention to disclose the MRI-based hazard screening method, comprising an additional step of selecting either one of the following: the fluid or the object as a fluid within the body of a living subject.

It is another object of the present invention to disclose the MRI-based hazard screening method, comprising an additional step of passing either one of the following: the fluid or the object from the body of a living subject, through the inlet and outlet, and returning it to the living subject It is another object of the present invention to disclose the MRI-based hazard screening method, for imaging at least one first and at least one second image features; comprising an additional step of adapting the image processor to render the image by a Boolean method of correlating or combining the at least one first and at least one second image features.

It is another object of the present invention to disclose the MRI-based hazard screening method, comprising an additional step of selecting the Boolean operators of the Boolean method from the group consisting of OR, AND, NOT, EXCLUSIVE OR and any combination thereof.

It is another object of the present invention to disclose the MRI-based hazard screening method, comprising an additional step of selecting either one of the following: the fluid or the object from a group consisting of potable water, sewage, irrigation water, sea water, river water, lake water, industrial effluent, farm effluent, effluent from human habitation, road runoff, blood, lymph, organic and/or inorganic flowable matter, a row material or product thereof, an animal product or part thereof, a plant product or part thereof, a biological fluid, a biological tissue, a tissue extract, an industrial fluid, a flowing food sample, a beverage, wine, milk, ketchup, cleaning fluid, and any combination thereof.

It is another object of the present invention to disclose the MRI-based method, additionally comprising a step of indicating the type of the contaminating particles within or on the surface of the object.

What is claimed is:

1. An MRI-based hazard screening system for detecting contaminating particles within or on the surface of an object, the system characterized by
   a. a sampling environment adapted for at least partially confining said object, said sampling environment is in fluid communication with at least one inlet and at least one fluid outlet;
   b. a fluid streamer for streaming a fluid, throughout said at least one inlet, towards said sampling environment where said fluid effectively interfaces said object; and further throughout said at least one outlet;
   c. an MRI device in fluid communication with said at least one outlet, adapted for providing an image of said particles streamed by said fluid thereby screening the presence of said particles within or on the surface of said object said MRI is provided for a high-resolution high-contrast imaging of said particles; said MRI comprising:
      i. at least one first magnet configured to provide a high magnetic field for generating multiple time-resolved one or more first images at high resolution of at least a portion of said fluid;
      ii. a least one second magnet configured to provide a low magnetic field for generating multiple time-resolved one or more second images at high contrast of at least a portion of said fluid; wherein at least one image of said first images and at least one image of said second images being generated in a time no greater than approximately the time between two first images; and
      ii. a CPU to process said images comprising a computer readable medium containing instructions for generating at least one third image superimposing at least one image of said first images with at least one image of said second images, whereby a high-contrast, high-resolution real-time continuous image of said fluid is obtained.

2. The MRI-based hazard screening system of claim 1, wherein a separator and/or a collector is in fluid communication with said at least one outlet, said separator and/or collector is adapted for one or more of the following: (i) separating out particles carried downstream by said fluid stream, and (ii) collecting said particles in a predefined volume of interest.

3. The MRI-based hazard screening system of claim 2, wherein at least one of the following is being held true (a) said MRI images said particles collected and accumulated in said volume of interest; (b) said separator is facilitated by means of a cyclone or filter or both; (c) said collector is facilitated by a particle collecting means selected from a group consisting of activated carbon, a filter including air filter, water filter, paper filter, HEPA filter, microfilter, water filter, water curtain, other conventional filter, other collection device, and any combination thereof.

4. The MRI-based hazard screening system of claim 1, wherein said fluid streamer is adapted for streaming a fluid in either continuously or batch-wise manner.

5. The MRI-based hazard screening system of claim 1, wherein at least one of the following is being held true (a) said at least one first magnet is of 2 Tesla and lower; (b) said at least one first magnet is of 2 Tesla and higher; (c) said at least one first magnet is selected from a group consisting of permanent magnets, electromagnets, superconducting magnets, and any combination thereof; (d) said at least one second magnet is of 2 Tesla and lower; (e) said at least one second magnet is of 2 Tesla and higher; (f) said at least one second magnet is selected from a group consisting of permanent magnets, electromagnets, superconducting magnets, and any combination thereof; (g) said at least one high magnetic field magnet is said at least one low magnetic field magnet; and any combination thereof.

6. The MRI-based hazard screening system of claim 1, wherein at least one of the following is being held true (a) an integrated MRI device comprises both said high magnetic field magnets and said low magnetic field magnets; (b) said high magnetic field magnets have a duty cycle greater than approximately 50% and said low magnetic fields magnets have a duty cycle less than approximately 50%; and any combination thereof.

7. An MRI-based hazard screening method for detecting contaminating particles within or on the surface of an object, comprising a. providing a sampling environment for at least partially confining said object; said sampling environment is in fluid communication with at least one inlet and at least one fluid outlet;
b. streaming a fluid, throughout said at least one inlet, towards said sampling environment where said fluid effectively interfaces said object; and further throughout said at least one outlet;
c. providing an MRI device in fluid communication with said at least one outlet;
d. generating an image of said particles streamed by said fluid thereby screening for the presence of said particles within or on the surface of said object;
e. providing a high-resolution high-contrast imaging of said particles; said step is carried out by the following steps:
  i. providing a least one first magnet configured to provide a high magnetic field for generating multiple time-resolved one or more first images at high resolution of at least a portion of said fluid;
  ii. providing at least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images;
  iii. providing a CPU to process said images comprising a computer readable medium containing instructions for generating at least one third image superimposing at least one image of said first images with at least one image of said second images;
  iv. generating multiple time resolved one or more first images at high resolution of at least a portion of said fluid;
  v. generating multiple time resolved one or more second images at high contrast of at least portion of said fluid; and
  vi. superimposing at least one image of said first images with at least one image of said second images; whereby a high-contrast, high resolution real-time continuous image of said particles streamed by said fluid is obtained.

8. The MRI-based hazard screening method of claim 7, comprising an additional step of providing a separator and/or a collector in fluid communication with said at least one outlet.

9. The MRI-based hazard screening method of claim 8, comprising one or more of the following steps: (i) separating out particles carried downstream by said fluid stream, and (ii) collecting said particles in a predefined volume of interest.

10. The MRI-based hazard screening method of claim 9, wherein at least one of the following is being held true (a) said method comprising an additional step of imaging said particles collected and accumulated in said volume of interest; (b) said method comprising an additional step of facilitating said step of separating by means of a cyclone or filter or both; (c) said method comprising an additional step of facilitating said step of collecting by a particle collecting means selected from a group consisting of activated carbon, a filter including air filter, water filter, paper filter, HEPA filter, microfilter, water filter, water curtain, other conventional filter, other collection device, and any combination thereof; and any combination thereof.

11. The MRI-based hazard screening method of claim 7, comprising an additional step of streaming said fluid in either a continuous or a batch-wise manner.

12. The MRI-based hazard screening method of claim 7, additionally comprising at least one step selected from a group consisting of (a) selecting said at least one first magnet to be of 2 Tesla and lower; (b) selecting said at least one first magnet to be of 2 Tesla and higher; (c) selecting said at least one first magnet from a group consisting of permanent magnets, electromagnets, superconducting magnets, and any combination thereof; (d) selecting said at least one second magnet to be of 2 Tesla and lower; (e) selecting said at least one second magnet to be of 2 Tesla and higher; (f) selecting said at least one second magnet from a group consisting of permanent magnets, electromagnets, superconducting magnets, and any combination thereof; (g) providing said at least one first magnet and said at least one second magnet as a single at least one magnet; (h) selecting an integrated MRI device comprising both said high magnetic field magnets and said low magnetic field magnets; (i) selecting a duty cycle for said high magnetic field magnets greater than approximately 50% and said low magnetic fields magnets have a duty cycle less than approximately 50%; and any combination thereof.

13. The MRI-based hazard screening method of claim 7, for imaging at least one first and at least one second image features; comprising an additional step of adapting said image processor to render said image by a Boolean method of correlating or combining said at least one first and at least one second image features.

14. The MRI-based hazard screening method of claim 13, comprising an additional step of selecting said Boolean operators of said Boolean method from the group consisting of OR, AND, NOT, EXCLUSIVE OR and any combination thereof.

* * * * *